United States Patent
Agrawal et al.

(10) Patent No.: US 11,449,779 B1
(45) Date of Patent: Sep. 20, 2022

(54) SOFTWARE SERVICE PLATFORM AND GRAPHICAL USER INTERFACE (GUI) FOR DETERMINING AND PRESENTING RULE-BASED CONCLUSIONS

(71) Applicant: Avalara, Inc., Seattle, WA (US)

(72) Inventors: Naveen Kumar Agrawal, Bellevue, WA (US); Marshal Kushniruk, Bainbridge Island, WA (US); Mark Wilhelm, Bainbridge Island, WA (US); Aaron David Wilson, Kenmore, WA (US)

(73) Assignee: AVALARA, INC., Seattle, WA (US)

( * ) Notice: Subject to any disclaimer, the term of this patent is extended or adjusted under 35 U.S.C. 154(b) by 189 days.

(21) Appl. No.: 16/875,633

(22) Filed: May 15, 2020

Related U.S. Application Data

(60) Provisional application No. 62/861,253, filed on Jun. 13, 2019.

(51) Int. Cl.
| | |
|---|---|
| *G06N 5/04* | (2006.01) |
| *G06N 20/00* | (2019.01) |
| *G06F 3/0482* | (2013.01) |
| *G06Q 30/00* | (2012.01) |
| *G06N 5/02* | (2006.01) |

(52) U.S. Cl.
CPC ............ *G06N 5/041* (2013.01); *G06F 3/0482* (2013.01); *G06N 5/02* (2013.01); *G06N 20/00* (2019.01); *G06Q 30/016* (2013.01)

(58) Field of Classification Search
CPC ........ G06F 3/0482; G06N 5/02; G06N 20/00; G06Q 30/016
See application file for complete search history.

(56) References Cited

U.S. PATENT DOCUMENTS

| | | | |
|---|---|---|---|
| 7,783,536 B2 | 8/2010 | William et al. | |
| 7,933,803 B1 | 4/2011 | Nadler et al. | |
| 8,620,578 B1 | 12/2013 | Brown et al. | |
| 8,725,407 B2 | 5/2014 | Hurley et al. | |
| 9,760,915 B2* | 9/2017 | Pavlou | G06Q 30/04 |
| 10,445,818 B1 | 10/2019 | Chowdhary | |
| 10,769,611 B2 | 9/2020 | McNeel | |
| 2004/0230525 A1* | 11/2004 | Barsade | G06Q 40/12 |
| | | | 705/40 |
| 2007/0136158 A1 | 6/2007 | Rawlings et al. | |
| 2007/0136159 A1 | 6/2007 | Rawlings et al. | |
| 2013/0013471 A1* | 1/2013 | Fishman | G06Q 40/00 |
| | | | 705/31 |
| 2017/0132603 A1* | 5/2017 | McNeel | H04W 4/02 |

\* cited by examiner

*Primary Examiner* — Cao H Nguyen
(74) *Attorney, Agent, or Firm* — Jeremiah J. Baunach; VLP Law Group, LLP

(57) ABSTRACT

Some embodiments of the present disclosure may relate generally to software-based service platforms and graphical user interface (GUI) architectures for determining and presenting rule-based conclusions, along with explanations identifying the factor or factors influencing the conclusions. Other embodiments may be disclosed and/or claimed.

14 Claims, 15 Drawing Sheets

FIG. 4

*(Screen interface showing invoice 100000000041)*

Top menu: Activities | Transactions | Lists | Reports | Analytics | Documents | Setup | Customization | Fixed Assets | Avalara | Support Buttons: Edit | Back | Authorize Return | Accept Payment | Credit | Renew | Actions Status: OPEN

- CUSTOMER
- CURRENCY: USA
- SUBSIDIARY: US - West
- DATE: 10/4/2019
- CONTRACT START DATA: 10/4/2019
- INVOICE #: 100000000041
- POSTING PERIOD: Oct 2019

- SALES REP
- PARTNER
- TERMS: Net 30
- DUE DATE: 11/3/2019
- PO #
- ACCOUNT: Accounts Receivable
- OPPORTUNITY
- SHIP-TO ENTITY/USE CODE (2)

Summary

| | |
|---|---|
| SUBTOTAL | 1,478.00 |
| DISCOUNT | |
| TAX ← 405 | 0.00 |
| SHIPPING COST | |
| HANDLING COST | |
| GIFT CERTIFICATE | |
| TOTAL | 1,478.00 |
| AMOUNT DUE | 1,478.00 |

┌─────────────────────────────────────────────────────────────────────┐
│ ⏱ ☆ 🏠 Activities | Transactions | Lists | Reports | Analytics | Documents | Setup | Customization | Fixed Assets | Avalara | Support │
│                                                                                              ─ 510                   │
│ 10000000041                                                                                                         │
│ [Edit] [Back] | [Authorize Return] [Accept Payment] [OPEN] [Credit] [Renew] | 📇 ⤵ ▸ Actions ▾                      │
│                                                                                                                     │
│ CUSTOMER                    SALES REP                    515 ┌──────────────────┐    Summary                        │
│                                                              │  TAX IS ZERO     │                                   │
│ CURRENCY                    PARTNER                          │  BECAUSE YOU ARE │    SUBTOTAL          1,478.00     │
│ USA                                                          │  NOT SET UP TO   │    DISCOUNT                       │
│ SUBSIDIARY                  TERMS                            │  COLLECT TAX IN WA│   TAX                    0.00    │
│ US - West                   Net 30                           │  STATE (AVALARA) │    SHIPPING COST                  │
│ DATE                        DUE DATE                         └──────────────────┘    HANDLING COST                  │
│ 10/4/2019                   11/3/2019                                                GIFT CERTIFICATE               │
│ ○ CONTRACT START DATA       PO #                                                     TOTAL            1,478.00     │
│ 10/4/2019                                                                                                           │
│ INVOICE #                   ACCOUNT                                                  AMOUNT DUE       1,478.00     │
│ 10000000041                 Accounts Receivable                                                                     │
│ POSTING PERIOD              OPPORTUNITY                                                                             │
│ Oct 2019                                                                                                            │
│                             SHIP-TO ENTITY/USE CODE (2)                                                             │
└─────────────────────────────────────────────────────────────────────┘

① ☆ 🏠 Activities | Transactions | Lists | Reports | Analytics | Documents | Setup | Customization | Fixed Assets | Avalara | Support

100000000041  ⟵ 520

[Edit] [Back] | [Authorize Return] [Accept Payment] [Credit] [Renew] | 🖨 | ⤴ Actions▾   OPEN

CUSTOMER                                       SALES REP

CURRENCY                                       PARTNER
USA

SUBSIDIARY                                     TERMS
US - West                                      Net 30
DATE                                           DUE DATE
10/4/2019                                      11/3/2019
◯ CONTRACT START DATA                          PO #
10/4/2019
INVOICE #                                      ACCOUNT
100000000041                                   Accounts Receivable
POSTING PERIOD                                 OPPORTUNITY
Oct 2019

SHIP-TO ENTITY/USE CODE (2)

525 ⟶ [IF WONDERING ABOUT THIS, <u>CLICK HERE</u>]

| Summary | |
|---|---|
| SUBTOTAL | 1,478.00 |
| DISCOUNT | |
| TAX | 0.00 |
| SHIPPING COST | |
| HANDLING COST | |
| GIFT CERTIFICATE | |
| TOTAL | 1,478.00 |
| AMOUNT DUE | 1,478.00 |

FIG. 5C

Avalara AvaTax UPDATE — 600

TRANSACTIONS ˅    EXEMPTIONS    RETURNS ˅    REPORTS      NAVEEN AGRAWAL ˅

| TEST-NAVEEN INC   Switch company | | | | | | | SETTINGS |

Transactions ⓘ     ⓘ Need help with this?

➕ Add transaction | ⬆ Import transactions | ⬇ Export transactions

FROM    TO
📅 01/01/2018    📅 02/05/2018    [Apply date range]    ✏ Update status of select[ed]

> You are not set-up to collect taxes in Washington State. Click here to learn more....

| ☐ DOC CODE → | DOC DATE → | DOC STATUS → | LOCATION CODE → | CUST/VENDOR CODE → | REGION → | AMOUNT → | NON-TAXABLE → | TAXABLE → | TAX → |
|---|---|---|---|---|---|---|---|---|---|
| ☐ DWA-101 | 02/05/2018 | Saved | | CWA-101 | WA | 1,000.00 | 1,000.00 | 0.00 | 0.00 |
| ☐ D101 | 01/11/2018 | Committed | | C101 | AL | 1,000.00 | 0.00 | 1,000.00 | 60.00 |

FIG. 6

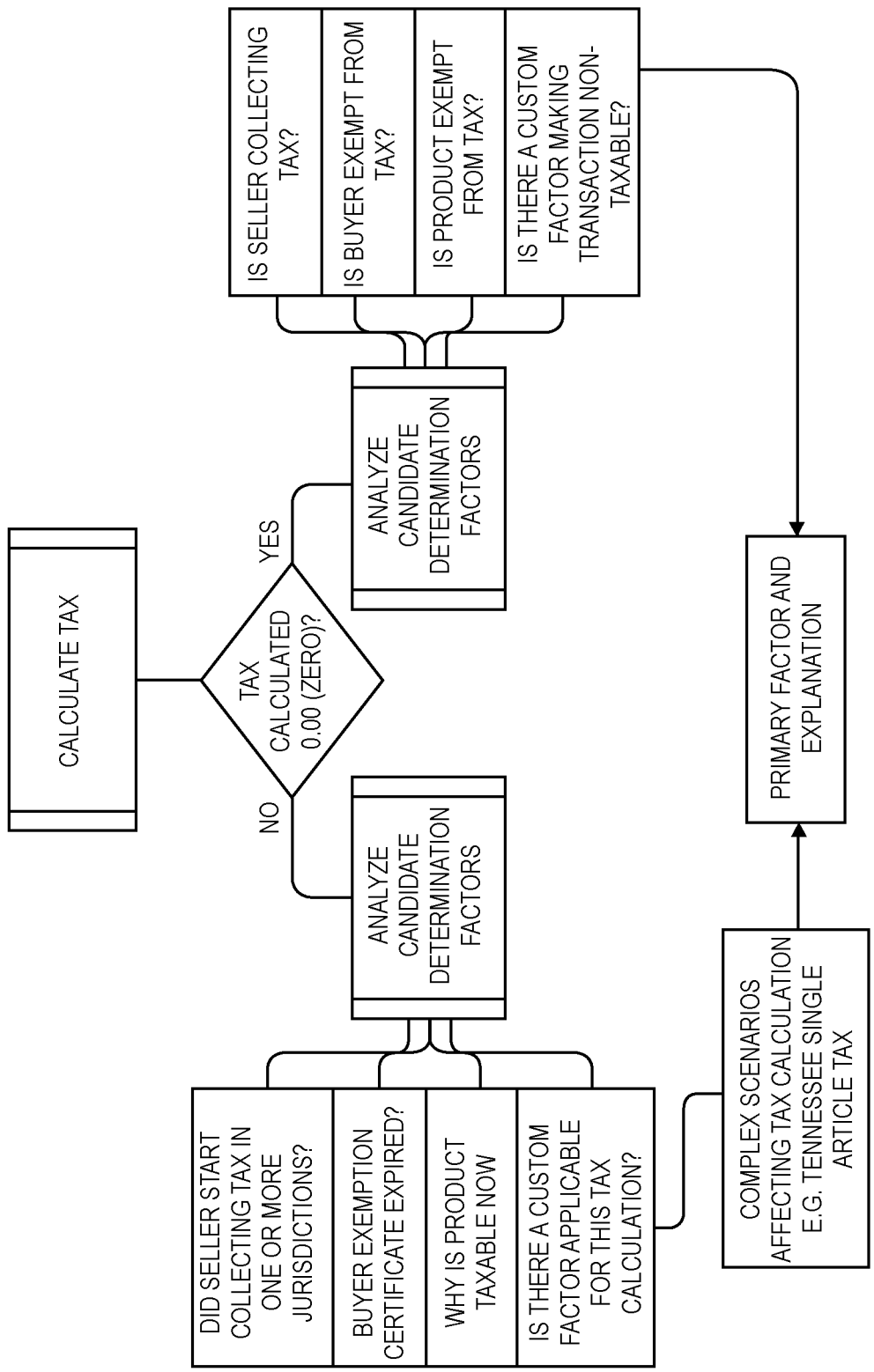

SOFTWARE SERVICE PLATFORM AND GRAPHICAL USER INTERFACE (GUI) FOR DETERMINING AND PRESENTING RULE-BASED CONCLUSIONS

CROSS REFERENCE TO RELATED APPLICATIONS

The present application claims priority to U.S. Provisional Patent Application No. 62/861,253, filed Jun. 13, 2019, entitled "ASSISTANT FOR CLOUD-BASED SERVICE," the entire content and disclosure of which is hereby incorporated by reference in its entirety.

BACKGROUND

Software applications are used in a variety of applications to determine and present conclusions to users. In many applications, however, there is a lack of transparency as to the manner in which a conclusion is determined. This can degrade the value of the conclusion to a user, and may cause an increased burden on "helpdesk" or other human-based support resources to handle questions regarding such conclusions from users.

Embodiments of the present disclosure address these and other issues by providing a software-based service platform and graphical user interface (GUI) architecture that helps determine and present rule-based conclusions along with explanations identifying the factor or factors influencing the conclusions.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which:

FIG. 4 illustrates an example of a conventional user interface associated with the process in FIG. 3.

FIGS. 5B and 5C depict examples of a user interface according to various embodiments of the present disclosure.

FIG. 6 depicts an example of a user interface according to various embodiments of the present disclosure.

FIGS. 7A-7F depict examples of functional block diagrams according to various aspects of the present disclosure.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Figure 1:
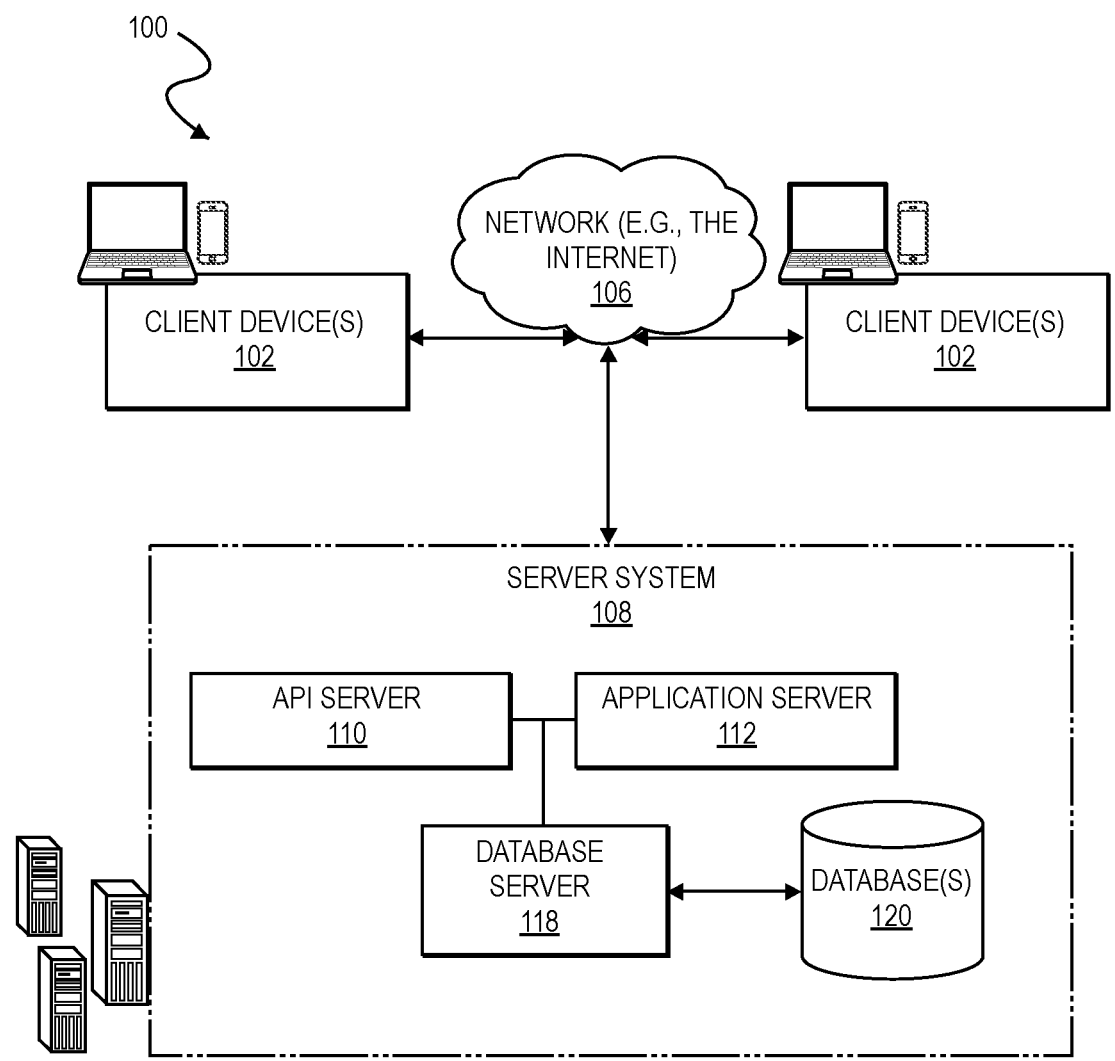
FIG. 1 is a block diagram showing an example of a system according to various embodiments of the present disclosure.

FIG. 1 is a block diagram showing an exemplary system 100 for exchanging data over a network. In this example, the system 100 includes multiple client devices 102, each of which may host a number of applications. In this context, a "client device" may refer to any machine that interfaces to a communications network to obtain resources from one or more server systems or other client devices. A client device may be, but is not limited to, a mobile phone, a desktop computer, a laptop, a portable digital assistant (PDA), a smart phone, a tablet, an ultra book, a netbook, a multi-processor system, a microprocessor-based or programmable consumer electronics device, a game console, a set-top box, or any other communication device that a user may use to access a network.

Each client device 102 may communicate and exchange data with other client devices 102, as well as with server system 108 via the network 106. Such data may include functions (e.g., commands to invoke functions) as well as payload data (e.g., text, audio, video or other multimedia data). In this context, the network 106 may be, or include, one or more portions of a network such as an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The server system 108 provides server-side functionality via the network 106 to one or more client devices (102). While certain functions of the system 100 are described herein as being performed by either a client device 102 or by the server system 108, it will be appreciated that some functionality may be interchangeably performed by either the client device 102 or by the server system 108. For example, it may be technically preferable to initially deploy certain technology and functionality within the server system 108, but later migrate this technology and functionality to a client device 102 having sufficient processing/memory capacity. Additionally, some functionality of embodiments of the present disclosure may be distributed across a plurality of different processors and/or computing devices, including one or more client devices 102 and server systems 108.

The server system 108 supports various services and operations that are provided to the client devices 102. Such operations include transmitting data to, receiving data from, and processing data generated by the client device 102. This data may include, for example, message content, client device information, geolocation information, database information, transaction data, social network information, and other information. Data exchanges within the system 100 are invoked and controlled through functions available via user interfaces (UIs) of the client devices 102.

In the example depicted in FIG. 1, system 108 includes an Application Programming Interface (API) server 110 that is coupled to, and provides a programmatic interface to, an application server 112. The API server 110 and application server 112 are communicatively coupled to a database server 118, which facilitates access to a database 120 including data that may be processed by the application server 112. In other embodiments, the functionality of the API server 110, application server 112, and database server 118 may be performed by more or fewer systems. In some embodiments, for example, server system 108 may comprise a single server having API functionality, application functionality, and database functionality.

In the example shown in FIG. 1, the API server 110 receives and transmits data (e.g., commands and message payloads) between the client device 102 and the server system 108. Specifically, the API server 110 provides a set of interfaces (e.g., routines and protocols) that can be called or queried by the one or more software applications running on a client device 102 in order to invoke functionality of the application server 112 or database server 118. The API server 110 exposes various functions supported by the application server 112, including account registration, login functionality, the sending of messages, search queries, and other functionality.

The application server 112 hosts a number of applications and subsystems. For example, the application server 112 may implement a variety of message processing technologies and functions, including various data-processing operations, with respect to data received within the payload of a message received from one or more client devices 102, or retrieved from one or more databases 120 by database server 118.

Software Service Platform and Graphical User Interface (GUI) for Determining and Presenting Rule-Based Conclusions As described in more detail below, embodiments of the present disclosure help determine and present rule-based conclusions along with explanations identifying the factor or factors influencing the conclusions. Additionally, embodiments of the present disclosure can help users. These rules may help with processing by a software service or software platform, such as the server system 108.

Figure 2:
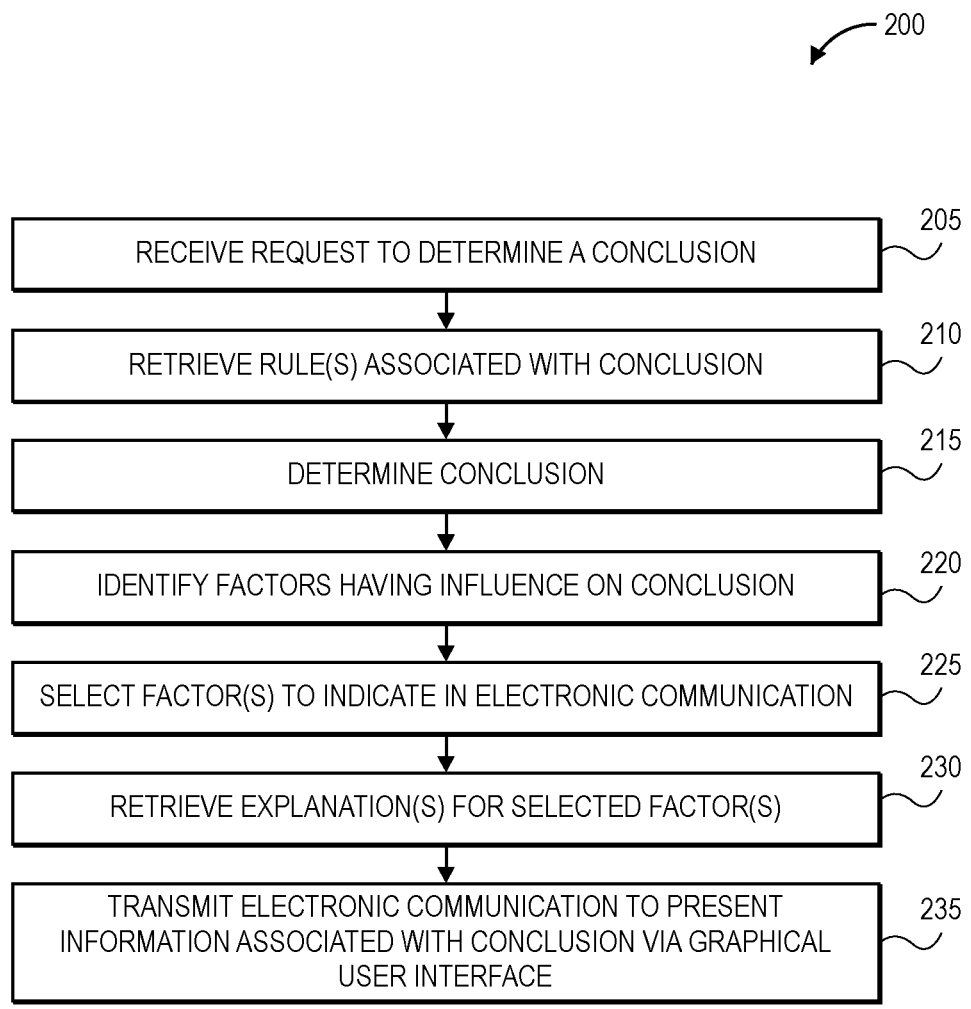
FIG. 2 is a flow diagram of an exemplary process according to various embodiments of the disclosure.

FIG. 2 depicts an exemplary process according to various aspects of the present disclosure, which may be performed by a server computer system, such as server system 108 in FIG. 1 and described above. In this example, method 200 includes receiving a first electronic communication that includes a request to determine a conclusion (205). Method 200 further includes retrieving one or more rules associated with determining the conclusion (210), determining the conclusion based on the one or more rules (215), identifying a plurality of factors having influence on the determination of the conclusion (220), and selecting one or more of the factors to indicate in a second electronic communication (225). The method further includes retrieving a respective explanation for each respective selected factor (230), and transmitting the second electronic communication to present information associated with the conclusion on a graphical user interface (GUI) of a client computing device (235). The steps of method 200 may be performed in whole or in part, in conjunction with each other as well as with some or all of the steps in other methods, and may be performed by any number of different systems, such as the systems described in FIGS. 1, 8, and 9.

Figure 3:
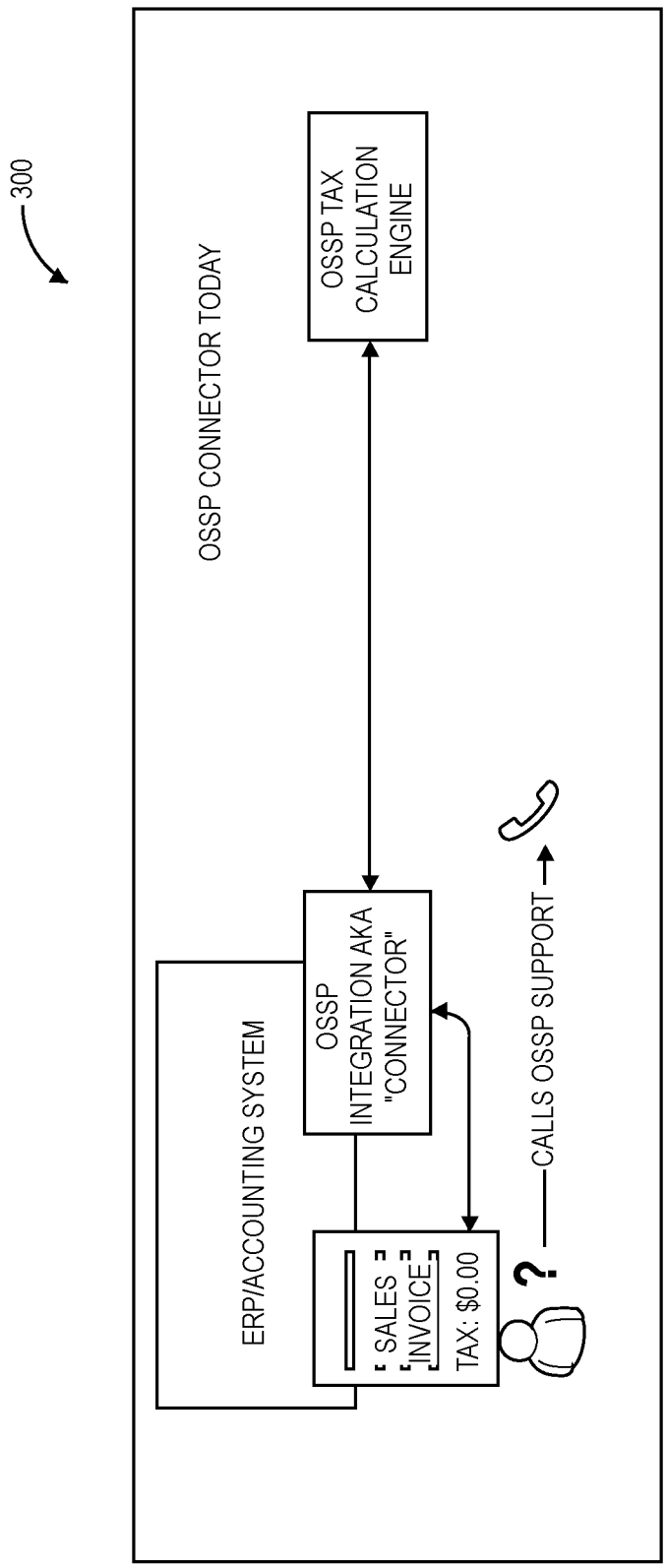
FIG. 3 depicts an exemplary functional block diagram of a conventional process.

FIGS. 3 and 4 illustrate an example of a use case illustrating a user interaction with a conventional system lacking the explanation features of the embodiments described herein. In this example, an ERP Accounting System has procured a conclusion for an invoice from an online software service platform (OSSP). Procuring has been by using an OSSP integration which, in this case, is a software connector. In particular, a user has previously transmitted an electronic communication to the online software service platform (OSSP), the communication including a request to determine a conclusion (the determination of sales tax in this example) along with data relevant to determining the conclusion. It should be noted that while some examples of embodiments in the present disclosure are illustrated with respect to the determination of conclusions such as taxes, other embodiments may be implemented in conjunction with the determination of a wide variety of different conclusions.

In FIG. 3, the OSSP, which may be implemented on a server computer system (such as server system 108 in FIG. 1) has received (e.g., over a network such as network 106 in FIG. 1) the request (205), has retrieved previously stored rules associated with the conclusion (210), and has determined the conclusion based on at least one of the stored rules and on the support data of the request (215), and has transmitted it to the user. FIG. 3 shows the user as puzzled about the conclusion, and contacting the OSSP support by telephone. FIG. 4 illustrates an example of a GUI that presents to the user the determined conclusion (sales tax calculation) 405 that was procured in the scenario of FIG. 3. In this example, the conclusion is presented in the GUI by itself, without any indication as to how or why the value ($0.00 sales tax due) was determined. In this scenario, the user of FIG. 3 may lack confidence that the sales tax conclusion determined by the OSSP is correct, and (as illustrated in FIG. 3) call the support line with questions regarding the conclusion such as: "why didn't you calculate tax on this invoice?" Such support calls often require significant time and resources to address, including time and effort spent by human support staff to resolve users' questions. As described below, embodiments of the present disclosure help reduce support calls by identifying factors associated with the determination of conclusions and retrieving and presenting explanations associated with the conclusions via the GUI itself.

Figure 5A:
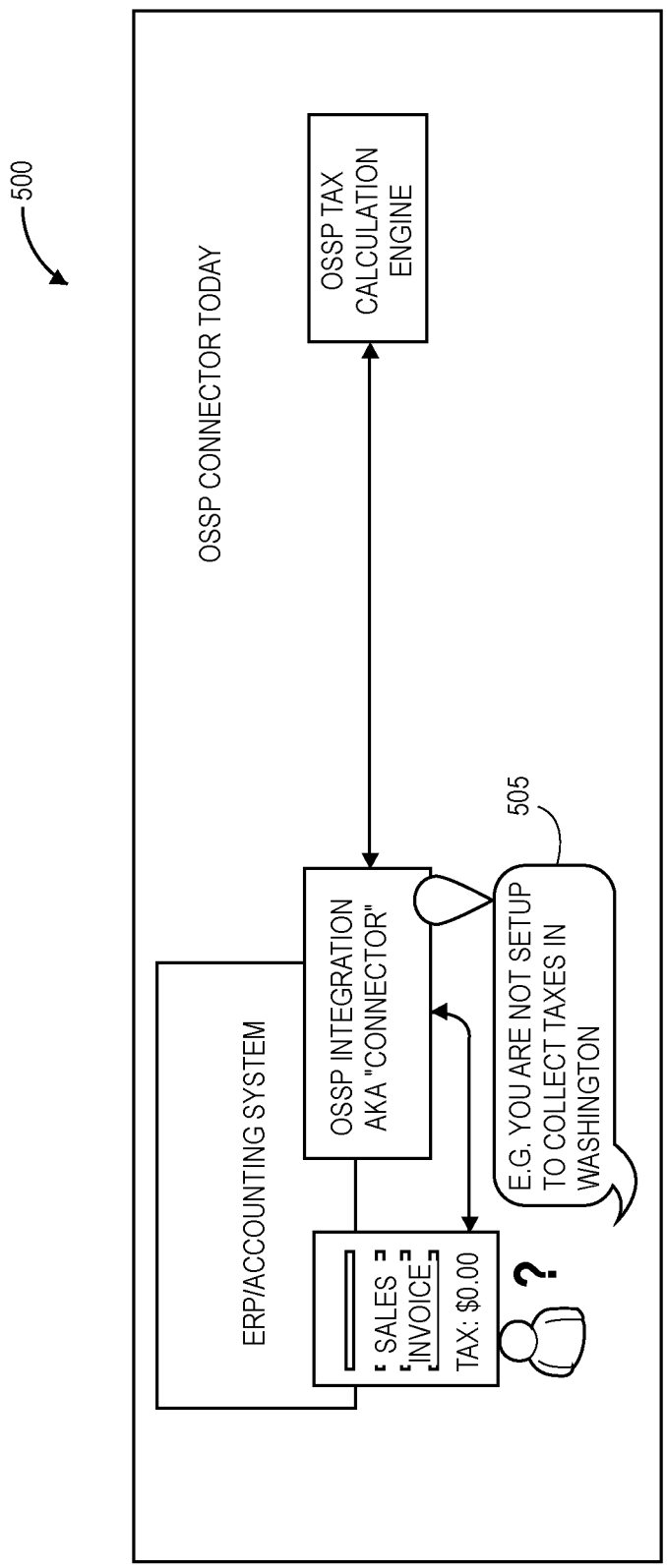
FIG. 5A depicts an exemplary functional block diagram of a process according to various aspects of the present disclosure.

FIGS. 5A and 5B illustrate a user interaction with a system implementing an embodiment of the present disclosure. FIG. 5A depicts an exemplary functional block diagram 500 of the interaction, and FIG. 5B depicts an example of a user interface 510 associated with the interaction.

In this example, the system performs steps 205, 210, and 215 similarly as described above for FIGS. 3 and 4. Additionally, the system identifies at least one factor having influence on the determination of the conclusion (220). Such factors may generally include, for example, any factor that led to the conclusion. The system may particularly select (225) one or more factors along with retrieving a respective explanation associated with each respective factor (230) to indicate to the user as being a salient aspect of the conclusion. For example, the system may select a factor and explanation that is likely to be most helpful (relative to other factors that may influence the conclusion) to the user in understanding the determination of the conclusion.

The system further transmits (e.g., over a network such as network 106 in FIG. 1) a second electronic communication (235) that includes a response to the request, in which the second electronic communication is configured to cause a client computing device receiving the response to display information associated with the conclusion via a GUI. In some embodiments, a first electronic communication that includes the request and data for determining the conclusion may be received from a first client computing device, and the second electronic communication transmitted to a second client computing device. In other embodiments, the system may receive the request and data from the same client computing device to which it transmits the response. In other embodiments, the system may transmit the response to multiple client devices to display the GUI on the respective display screens of each client device (such as client device 102). In alternate embodiments, the system may display the GUI on a display screen coupled to the system itself.

The response may include, and cause the GUI on a client device to display, a variety of information associated with the conclusion. For example, such information may include one or more of: an indication of the conclusion, and at least one of an indication of the selected one or more selected factors, and an indication of the one or more explanations associated with the one or more selected factors.

In the example illustrated in FIGS. 5A and 5B, the system selects one factor (indicated as the "primary factor") having influence on the determination of a $0.00 sales tax, along with a text explanation 505 that indicates that the user is not set up to collect taxes in Washington state. In FIG. 5B, the explanation 515 is presented simultaneously with the sales tax conclusion, thus providing the user with information on how and why the conclusion was so determined, and helping to avoid the support call from the user illustrated in FIGS. 3 and 4.

In some embodiments, presenting the GUI includes displaying the indication of the explanation, the indication of the factor, and the indication of the conclusion together simultaneously on the display screen. In other embodiments, presenting the GUI may include displaying the indication of the conclusion and a selectable link that, when selected by a user (e.g., of the client computing device upon which the GUI is displayed), displays at least one of the indication of the one or more explanations and the indication of the one or more factors in conjunction with the indication of the conclusion on the display.

In some embodiments, the second electronic communication may further include information associated with the determination of the conclusion, and presenting the GUI may include displaying the indication of the one or more explanations and the indication of the one or more factors in conjunction with a selectable link that, when selected by a user of the second client computing device, displays the information associated with the determination of the conclusion on the display screen. In one example, a hyperlinked prompt may be provided together with the conclusion, the prompt including words to the effect of: "wondering about this?", and clicking on the prompt reveals the explanation simultaneously with the conclusion in the GUI.

In some embodiments, at least a certain one of the presented explanations includes a proposed remedy for the event that the factor associated with the certain one of the presented explanations is undesirable to a user of the display screen. For example, the indication of the one or more explanations may be displayed in conjunction with a selectable link that, when selected by a user, presents an option to modify a setting associated with the proposed remedy on the display screen.

In one example, referring now to FIG. 5C, a GUI 520 presents a link 525 that, when selected, presents a more detailed explanation regarding how the conclusion was determined. In some embodiments the more detailed explanation may be displayed in the same GUI page as the conclusion. In other embodiments, the detailed explanation may be presented in a separate display page.

FIG. 6 illustrates an example of a GUI page presenting [[the]] an "existing transactions" view. In this example, GUI 600 includes a text box indicating the explanation and a link to allow the user to access more detailed information regarding the determination of the conclusion.

In some embodiments, the OSSP may employ an algorithm to determine what query a user is likely to have for a given conclusion to, in turn, help retrieve an explanation most likely to answer to the user's query. In some embodiments, the system may utilize machine learning based on data gathered as conclusions are determined and explanations provided for a variety of conclusions to help improve the algorithm and better identify questions a user is likely to have for a given conclusion or category/type of conclusion.

In some embodiments, identifying the plurality of factors includes determining, for each respective factor in the plurality of factors, a respective weight associated with the respective factor's influence on the conclusion relative to the other factors in the plurality of factors. In some cases, the system may select a factor from the plurality of factors having the highest weight (e.g., the "primary factor"). In some embodiments, the system may select a subset of factors from the plurality of factors based on the weights of the factors in the subset, in which each of the selected factors in the subset have a higher weight than any unselected factor in the plurality of factors.

Referring again to the previous examples where the sales tax was calculated to be zero, then the system may determine that the most likely question a user may have is why zero tax was indicated. In some embodiments, the OSSP may evaluate determination data based on a list of candidate determination factors about why tax was not calculated, determine from the list of candidate determination factors the primary factor, and then provide the user with the explanation associated with the primary factor.

Determining a primary factor (or set of factors) from a list of candidate determination factors can be performed in an number of different ways. In some embodiments, for example, a primary factor may be determined using scoring based on a user's tax profile settings, transaction data, jurisdictional rules and various other data.

In some embodiments, the system may present the primary factor, and/or an explanation related to the primary factor, to a user. The explanation can be plain user-friendly text explaining what influenced determination primarily. In some embodiments the system may determine whether or not to display the primary factor based on user's settings. For example, the user may select to have the explanation always displayed, or only displayed in scenarios having a complexity score that is above a predetermined threshold. Such a complexity score may be determined in a number of ways, e.g., determined by the OSSP's algorithm based on the user's likely queries associated with a conclusion, and so on. In some embodiments, the OSSP may provide the explanation based on the primary factor alone, or the explanation may be constructed from various determination factors based on determination scenarios, as well as the user's settings.

Continuing the sales tax examples from above, the system may provide an explanation giving the reason(s) why the sales tax amount was calculated to be zero for a transaction, such as: the user is not set up to collect tax in a particular tax jurisdiction; a customer of the user is exempted because of a valid exemption certificate on file; or an item is mapped to a non-taxable tax code or item is non-taxable in the jurisdiction.

In some embodiments, the system may also determine the applicability of complex scenarios associated with the determination of the conclusion. In the sales tax examples presented previously, such scenarios may include jurisdiction-specific complex scenarios, such as: Tennessee single article tax @x % was applied, or Florida bracket tax calculation applied.

In some embodiments, the system may utilize machine learning to train the algorithm to respond to particular situations. In the tax examples, for instance, such situations may include situations where more than one tax type was calculated and what caused it. The OSSP may improve its algorithm using machine learning to analyze customer support case data and various other parameters used to determine the weight of a likelihood indicator.

In some embodiments, for example, a weight for a respective factor may be determined based on identifying a plurality of likelihood indicators associated with the respective factor, determining a respective weight for each respective likelihood indicator, and determining the weight for the respective factor as the sum of the weights determined for each respective likelihood indicator.

Figure 7A:
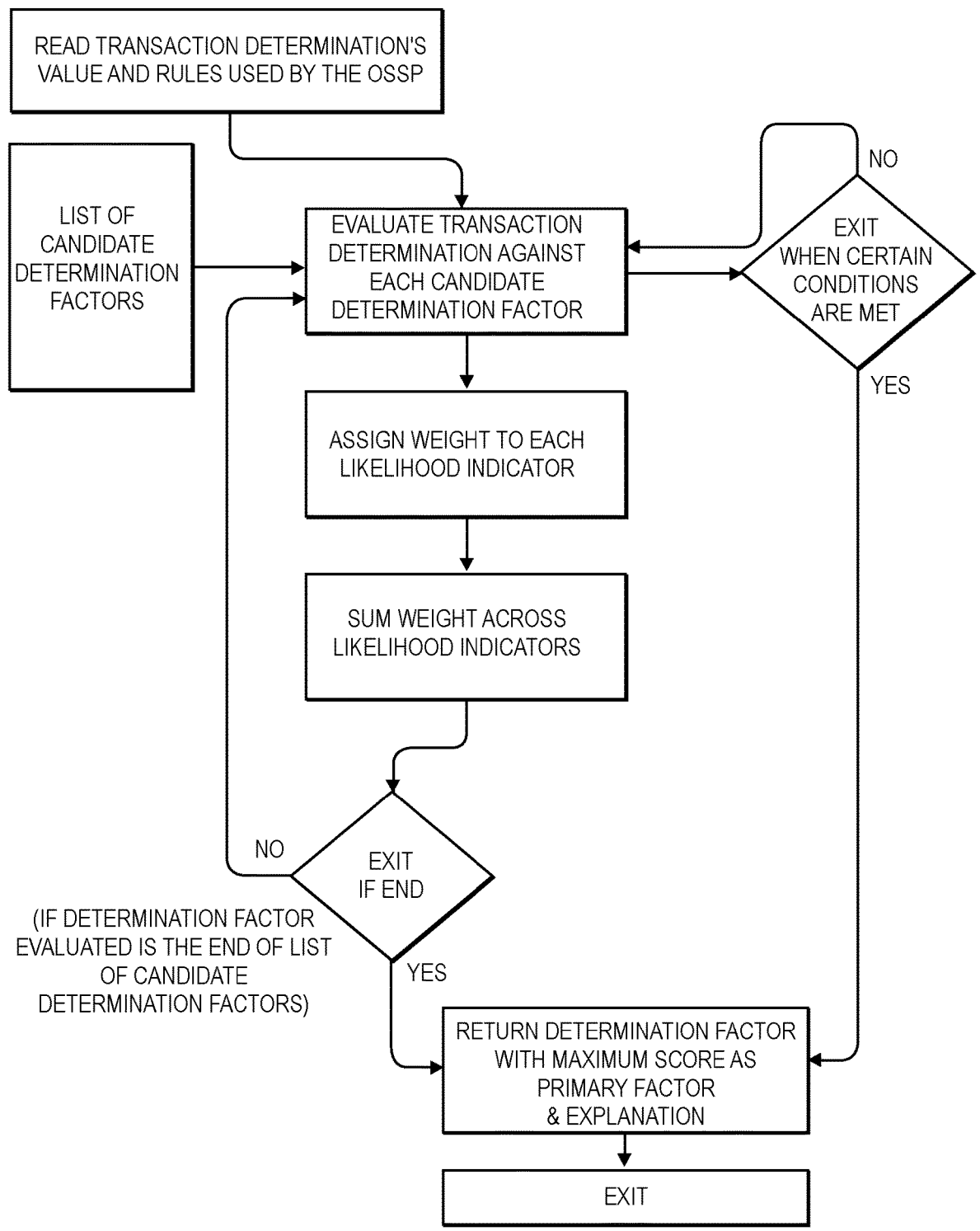

FIG. 7A illustrates an example of a flow diagram for a process to determine a primary factor in accordance with various embodiments. In this example, an algorithm evaluates a given transaction against a list of candidate determination factors in the order of evaluation sequence and assigns a score for each likelihood indicator. In this example, the weights across likelihood indicators for each candidate determination factor are added together, and this sum of weights across likelihood indicators is referred to as the "score." In this example, the algorithm will return the determination factor with maximum score as the primary factor.

The OSSP may use a data structure storing the explanations, and return the explanation associated with the primary factor to the user. In cases where multiple determination factor are to be displayed, the OSSP may return an explanation which describes all the determination factors with a positive score.

As illustrated in FIG. 7A, values and rules for the desired conclusion (the conclusion is referred to as a "determination" in this example) are input, along with a list of candidate determination factors. The system determines, based on the value and rules used, which of the candidate determination factors were used in determining the conclusion. In some cases the algorithm may optionally exit the loop for certain conditions.

The system assigns weights to each likelihood indicator, and sums the weights across likelihood indicators for a candidate determination factor. The algorithm exits if the determination factor was the last factor in the list of candidate determination factors, otherwise the steps repeat for all candidate determination factors. Once all candidate determination factors are processed, the algorithm selects the determination factor with the maximum score and returns it as the primary factor.

The system may optionally look up an explanation for the primary factor, and may optionally look up remedy recommendations for the primary factor. the output of the algorithm is the primary factor and its associated explanation. As illustrated above, the formula to calculate the score is thus the sum of the weight assigned to each likelihood indicator for a determination factor.

Figure 7B:
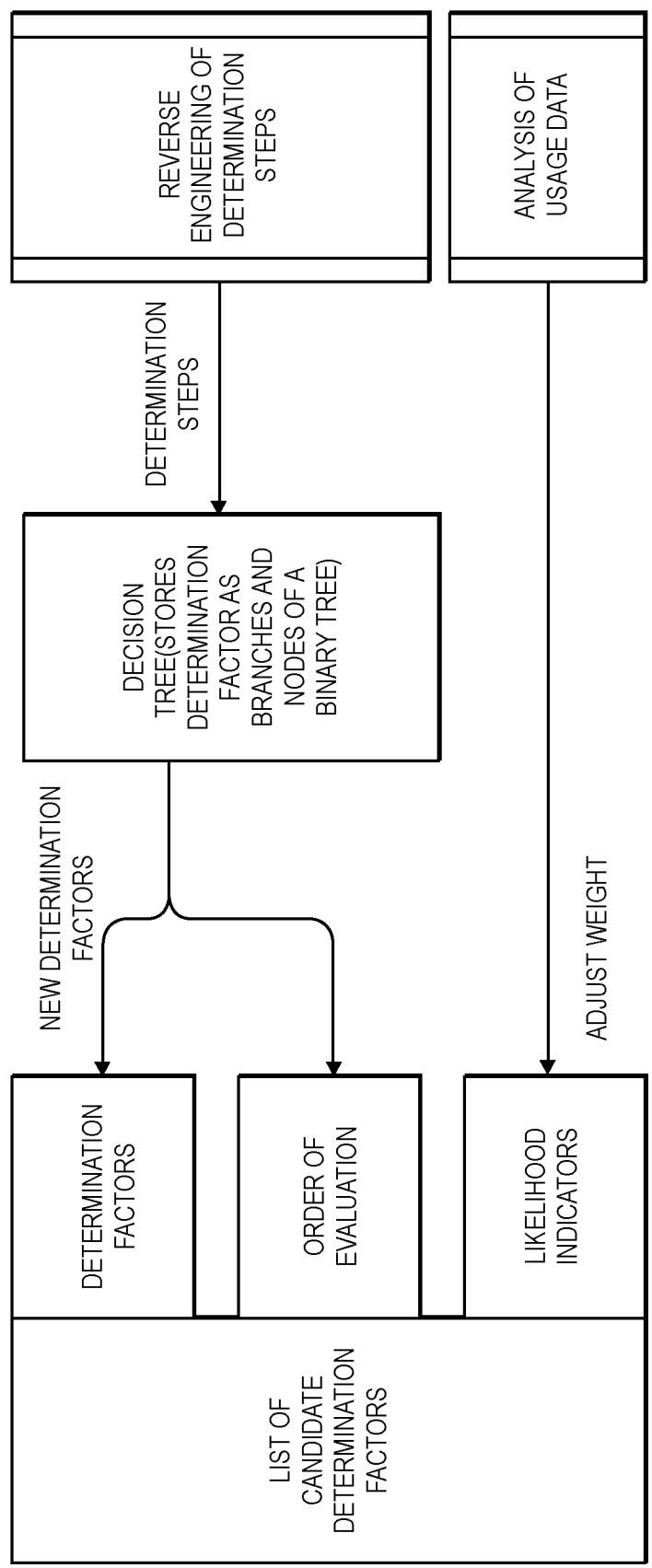

FIG. 7B illustrates an example of various data structures that may be utilized by the algorithm illustrated in FIG. 7A. In this example, a data structure includes a list of determination factors. An order of evaluation is assigned to each determination factor, and likelihood indicators with weights are associated with each determination factor.

Figure 7C:
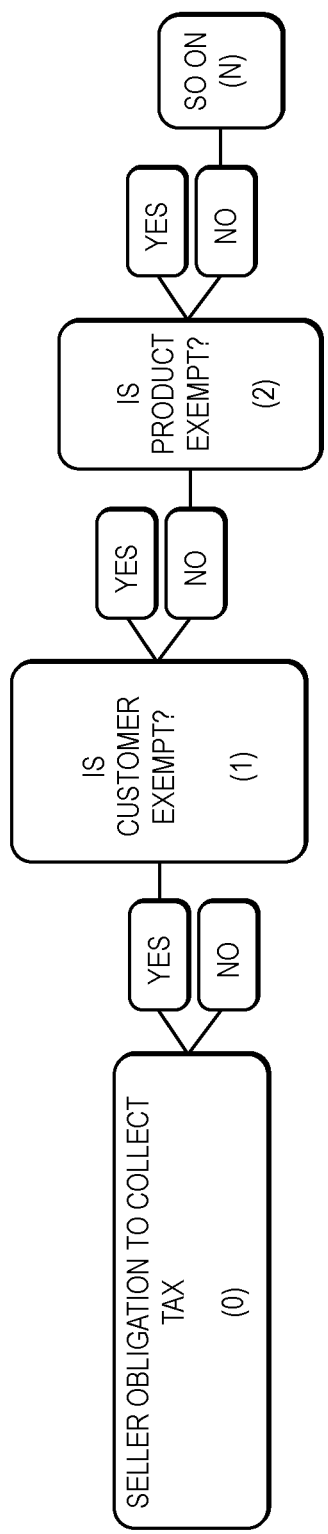

In some embodiments, the list of candidate determination factors can be maintained by the OSSP to add new determination factors as well as adjusting the weight of likelihood indicators based on new user interaction data. In some embodiments, the order of evaluation is based on a decision tree which, in turn, will feed the number of nodes as the order of evaluation in the list of candidate determination factors data structure. An example of a decision tree is illustrated in FIG. 7C. In some embodiments, the system may utilize machine learning to create and modify decision trees used by the algorithm (e.g., to add, remove, or modify steps in a decision tree) based on steps added to existing determination scenarios or the addition of new determination scenarios in the OSSP.

In some embodiments, the likelihood indicators may be used to indicate a probability that a likelihood indicator will provide an explanation to one or more questions the user will have upon viewing a conclusion. These likelihood indicators may be assigned a weight to evaluate their influence on a given conclusion/determination.

For instance, the following are some examples of likelihood indicators for determining a sales tax use case:

Zero tax vs Non-Zero tax determination reasons—Users often wonder when there was no tax calculated and that happens due to a number of reasons. Whereas if a non-zero tax amount was calculated, users are looking for a different explanation.

Historical Customer support case data—Over time, the questions asked by the OSSP's users can be stored and tracked such that the OSSP knows when and how often a particular question is likely to be asked.

Complex determination scenarios—There are tax calculation scenarios where a standard tax calculation logic doesn't justify the tax amount calculated. In such scenarios, a user usually needs more explanation with respect to jurisdiction and product taxability specific sales tax collection laws and/or the explanation for a specific mathematical formula applied.

Customer's tax profile settings—The OSSP's customers, who can be sellers, can configure their business profile that governs the tax calculation as well. They may not clearly understand the impact of their business profile setup on calculation and as a result wonder why the OSSP calculated or didn't calculate a particular tax.

User novelty—How familiar a user is with the OSSP's software would also be considered. Users experienced with the OSSP's tax software and sales tax compliance in general look for answers on more complex scenarios than users less familiar with the OSSP's tax calculation software and tax compliance laws.

Each determination factor may be weighted across multiple likelihood indicators which indicate how likely a user is going to query about this factor. For example, in Table 1 below, a likelihood indicator "Weight for user novelty" will be scored as per following logic:

IF historical data tells that this determination factor is queried mostly by users who have spent less than 1 year with the OSSP's software then it will get weight of 1

ELSE IF historical data suggests that this determination factor is usually queried by experienced users who have been using the OSSP's platform for more than 1 year, then it will get a weight of 0.5

ELSE IF historical data suggests that this determination factor is queried by both types of users equally, then it will get a weight of 0.

Similarly, all other likelihood indicators will be given a weight score. Additionally, the weight for various likelihood indicators may be adjusted via machine learning based on analysis of OSSP's software usage data over the period of time.

TABLE 1

List of Candidate Determination Factors with order of evaluation and likelihood indicators

| Determination Factor | Order of evaluation | Weight for Customer Support call reasons | Weight for Zero Tax vs Non-Zero tax Scenarios | Weight for complexity | Weight for tax profile settings | Weight for User Novelty |
|---|---|---|---|---|---|---|
| Determination Factor 1 e.g. Seller is NOT registered to collect tax in given jurisdiction | 1 | 1 | 1 | 0 | 1 | 1 |
| Determination Factor 2 | 2 | 0.5 | 1 | 0.5 | 0 | 1 |
| Determination Factor N | N | 1 | 0 | 1 | 0 | 0.5 |

Figure 7D:
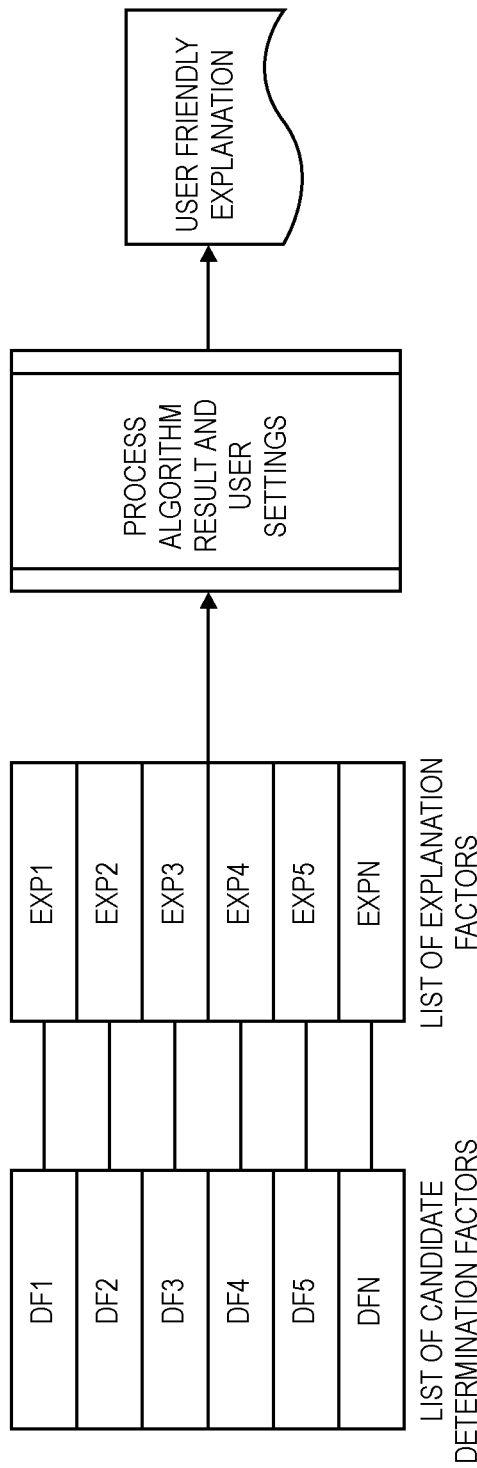

In some embodiments, a list of candidate determination factors is associated with a list of explanation factors. These explanation factors may be used to determine an explanation. The system may also consider user settings as well as the result of the algorithm to return an explanation that includes a single factor influencing the conclusion (e.g., a primary factor) or a plurality of factors which had an impact on the conclusion/determination. FIG. 7D illustrates an example of a list of explanation factors associated with determination factors for determining an explanation.

In some particular examples regarding the determination of tax-related conclusions, the following illustrates some examples of primary factors and their associated explanations:

| PRIMARY FACTOR | EXPLANATION |
|---|---|
| State Tax rate = 0 | "This state has a tax holiday now." |
| Item tax rate = 0 | "This item is mapped to a non-taxable tax code", or "This item is not taxable in this state." |
| No Setting for sales tax | "You are not setup to collect tax in that State - click here if you want to explore whether you haved eveloped economic nexus with it." |
| User tax rate = 0 | "Your buyer is exempted from paying tax because they have a valid exemption certificate on file." |

Figure 7E:
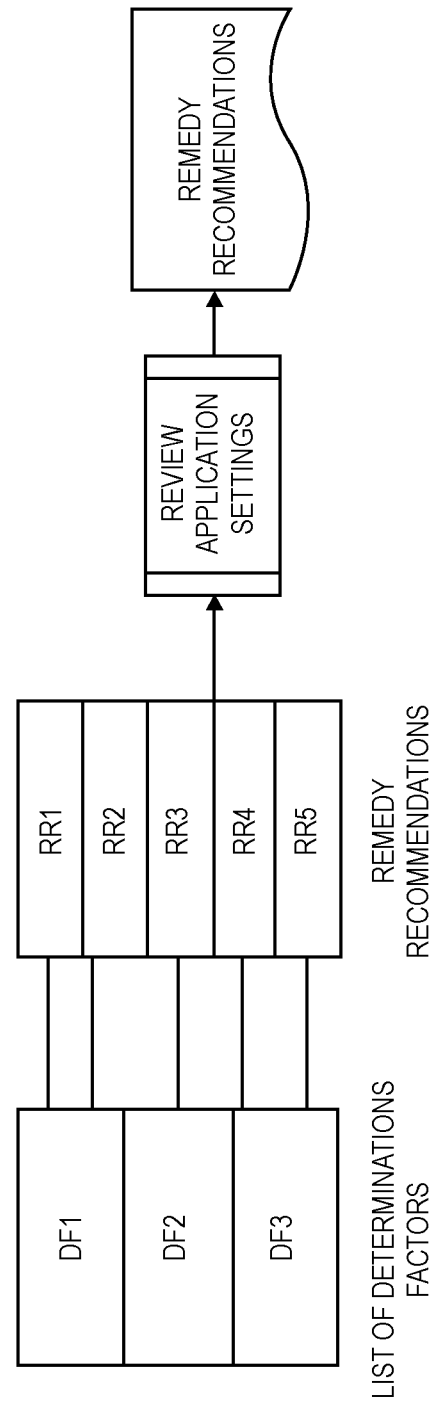

In some embodiments, the OSSP will also return remedy recommendations based on application settings and user interaction. For example, after receiving the explanation for a primary factor which impacted a tax calculation conclusion the most, the user may want to adjust one or more transaction determination inputs and/or business profile settings so that the OSSP will result in a different conclusion/determination. In order to do so, the user may be made aware of possible remedies available to the user. In some embodiments, each determination factor may be associated with one or more remedy recommendations. The system may retrieve the associated remedy recommendations and return them to the user based on application settings. FIG. 7E illustrates an example of providing remedy recommendations in accordance with various embodiments.

In a particular example of determining a sales tax conclusion, consider that the OSSP indicates an explanation that no tax was determined on a transaction because the user is not setup to collect taxes in the given jurisdiction. In this example, when the user receives the explanation, the user realizes that he/she must make an election for tax collection in the given jurisdiction. In this case, one of the remedy recommendations provided will be to tell the user where to go in the OSSP's software and change the settings to collect tax in the given jurisdiction and then recalculate the taxes on given transaction.

In some embodiments, where the conclusion/determination includes a computation, the result of the conclusion may include a number. In such cases, the primary factor could be an equation setting a value, while the explanation can be a sentence.

The following illustrates the determination of a conclusion (sales tax in this particular example) in accordance with embodiments of the present disclosure:

Does the determined sales tax equal zero?
If yes, the primary factor is determined to be the factor that caused the determined sales tax to equal zero (e.g. something that multiplied by zero). The OSSP may conclude this is the primary factor.
If NO, then try other candidate determination factors:
Option 1: try the other candidate determination factors according to the order of evaluation; pick the first one in the sequence that is true; apply AI to vary the order and weight of determination factors; or
Option 2: determine all such possible candidate determination factors that are true in this case; score them according to likelihood indicators.
Sample such sequence:
Is it true that the selling customers' customer, namely the buyer, had an exemption certificate, but which has expired?
If YES, Explanation: "Here your buyer had an exemption certificate, but it has expired; click here to notify them."
If NO: Was more than one tax type was calculated?
If YES, Explanation: "Here more than one tax type was calculated, because . . . "
If NO: State=? Tennessee;
If YES, Explanation: "Tennessee single article tax @x % was applied"
If NO: State=? Florida;
If YES, Explanation: "Florida bracket tax calculation applied . . . "

FIG. 7F illustrates an example of a process flow diagram for performing the sales tax calculation use case depicted above. For example, a sales tax calculation in the United States depends on a number of factors—one of them being whether a seller is required to and therefore chose to collect sales tax in a given jurisdiction or not. If the seller is collecting tax in a given jurisdiction, the sales tax amount is calculated per the jurisdictional tax rates for a given product. However, there could be other factors impacting this calculation, for example, a buyer may be entitled for exemption from sales tax, or a product may be either exempted or charged tax at a reduced rate when it meets certain conditions of its use.

In one particular example, consider a scenario where a user calculates sales tax on a sales order using the OSSP's tax calculation service and notices that tax amount indicated was $0.00 (zero). Therefore, the user is likely wondering (and wants to know) why there wasn't any sales tax calculated on this sales order.

The OSSP's algorithm to determine the likely query reads the determination data for the transaction and the rules used by the OSSP to determine the sales tax amount. Then it evaluates it against the list of candidate determination factors. For this example, Table 1 (above) illustrates a list of determination factors that may be used in conjunction with determining the tax.

In Table 1, "Determination Factor 1" (whether the seller is registered to collect tax in a given jurisdiction) is evaluated. The determination data contains "No" for this factor. As a result, all likelihood indicators except weight for complexity gets "1" and per the decision tree illustrated in FIG. 7C, when this factor gets a NO it ends the tree. Accordingly, no other determination factor will be applicable for this transaction, hence this determination factor gets the maximum score and this determination factor is returned as the primary factor. The OSSP returns an explanation associated with this determination factor which reads "You are not setup to collect tax in given jurisdiction."

In another example, consider a scenario where the state of Tennessee applies Single Article Tax on the sale of any single item of tangible personal property between $1600.01 and $3200.00. In this scenario, regular local option tax is applied to the first $1600 of the sale, and another state-wide tax is applied to the second $1600.00.

The OSSP determines tax on such a transaction using jurisdictional rules for Tennessee state. As a result, the user notices two state tax lines calculated on transaction. Therefore, the user is likely to wonder why state tax has been calculated twice. The algorithm will read the determination response and find two state lines, as well as the Tennessee State Single Article Tax Rule that was used.

As a result, when the system will run across the List of Candidate Determination Factors, it will find the determination factor called "Tennessee State Single Article Tax". This factor will get weight assignment across likelihood indicators. And then algorithm will sum the weights across all likelihood indicators for each determination factor.

In this scenario, due to complexity and the volume of customer support call reasons, this determination factor will get the maximum score. The Algorithm will return the determination factor "Tennessee Single Article Tax" as the primary factor.

In some embodiments, the display of the information may be based on settings controlled by a user. For example, the user may selectively turn the explanation feature on and off. In some embodiments, the user may selectively display explanations for different types or categories of conclusions. For instance, using the sales tax calculation example above, the user may turn off explanations for sales tax conclusions for California invoices, but turn on explanations for sales tax conclusions for Washington invoices.

Software and System Architectures

Figure 8:
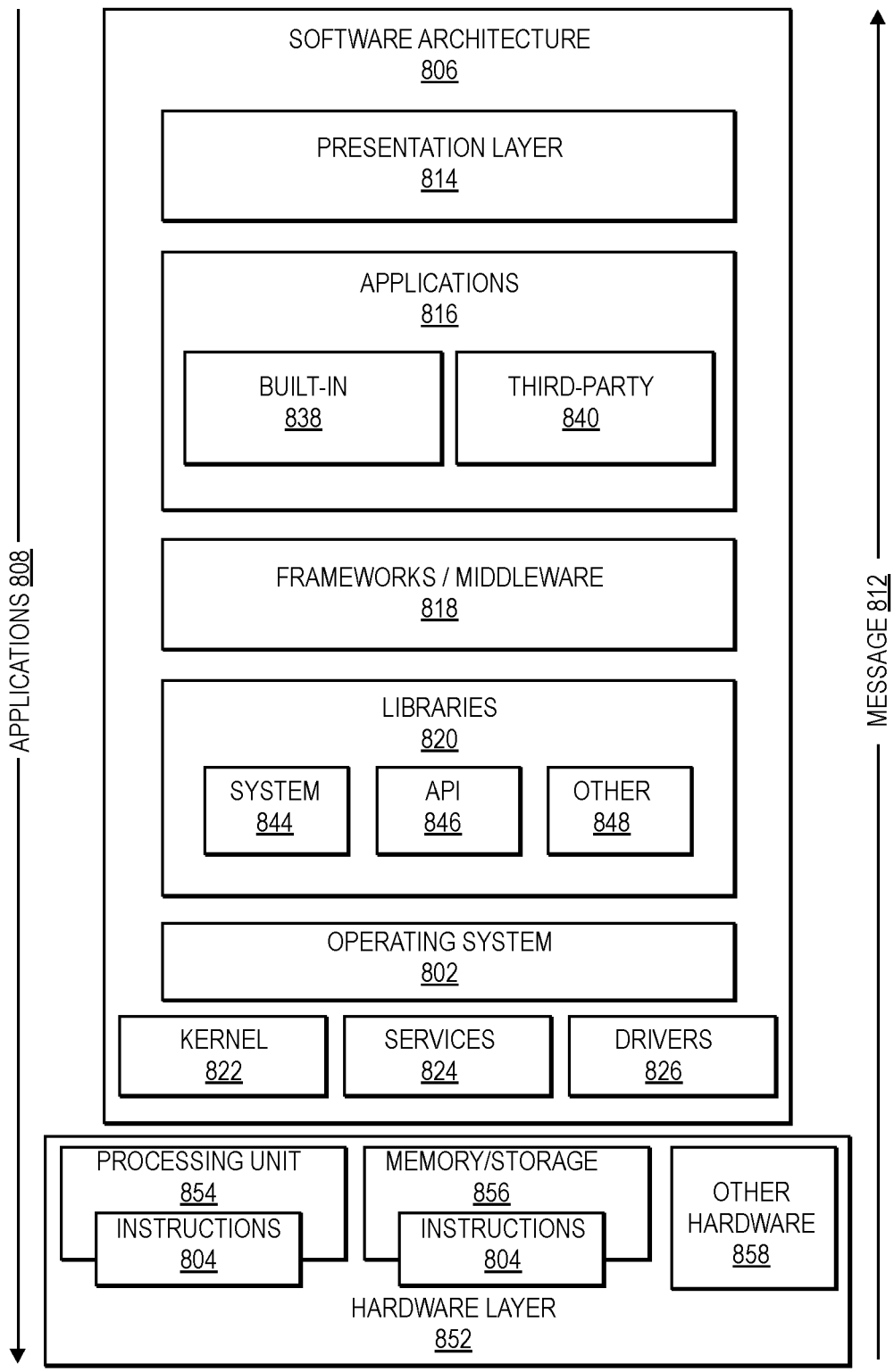
FIG. 8 is a block diagram illustrating an exemplary software architecture which may be used in conjunction with various hardware architectures herein described.

FIG. 8 is a block diagram illustrating an exemplary software architecture 806, which may be used in conjunction with various hardware architectures herein described. FIG. 8 is a non-limiting example of a software architecture and it will be appreciated that other architectures may be implemented to facilitate the functionality described herein. The software architecture 806 may execute on hardware such as machine 900 of FIG. 9 that includes, among other things, processors 904, memory 914, and I/O components 918. A representative hardware layer 852 is illustrated and can represent, for example, the machine 900 of FIG. 9. The representative hardware layer 852 includes a processing unit 854 having associated executable instructions 804. Executable instructions 804 represent the executable instructions of the software architecture 806, including implementation of the methods, components and so forth described herein. The hardware layer 852 also includes memory and/or storage modules memory/storage 856, which also have executable instructions 804. The hardware layer 852 may also comprise other hardware 858.

As used herein, a "component" may refer to a device, physical entity or logic having boundaries defined by function or subroutine calls, branch points, application program interfaces (APIs), or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various exemplary embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled.

Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of exemplary methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)). The performance of certain of the operations may be distributed among the processors, not only residing within a single machine, but deployed across a number of machines. In some exemplary embodiments, the processors or processor-implemented components may be located in a single geographic location (e.g., within a home environment, an office environment, or a server farm). In other exemplary embodiments, the processors or processor-implemented components may be distributed across a number of geographic locations.

In the exemplary architecture of FIG. 8, the software architecture 806 may be conceptualized as a stack of layers where each layer provides particular functionality. For example, the software architecture 806 may include layers such as an operating system 802, libraries 820, applications 816 and a presentation layer 814. Operationally, the applications 816 and/or other components within the layers may invoke application programming interface (API) API calls 808 through the software stack and receive responses to the API calls 808. Various messages 812 may be transmitted and received via the applications 816 and/or other components within the layers. The layers illustrated are representative in nature and not all software architectures have all layers. For example, some mobile or special purpose operating systems may not provide a frameworks/middleware 818, while others may provide such a layer. Other software architectures may include additional or different layers.

The operating system 802 may manage hardware resources and provide common services. The operating system 802 may include, for example, a kernel 822, services 824 and drivers 826. The kernel 822 may act as an abstraction layer between the hardware and the other software layers. For example, the kernel 822 may be responsible for memory management, processor management (e.g., scheduling), component management, networking, security settings, and so on. The services 824 may provide other common services for the other software layers. The drivers 826 are responsible for controlling or interfacing with the underlying hardware. For instance, the drivers 826 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 820 provide a common infrastructure that is used by the applications 816 and/or other components and/or layers. The libraries 820 provide functionality that allows other software components to perform tasks in an easier fashion than to interface directly with the underlying operating system 802 functionality (e.g., kernel 822, services 824 and/or drivers 826). The libraries 820 may include system libraries 844 (e.g., C standard library) that may provide functions such as memory allocation functions, string manipulation functions, mathematical functions, and the like. In addition, the libraries 820 may include API libraries 846 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 820 may also include a wide variety of other libraries 848 to provide many other APIs to the applications 816 and other software components/modules.

The frameworks/middleware 818 (also sometimes referred to as middleware) provide a higher-level common infrastructure that may be used by the applications 816 and/or other software components/modules. For example, the frameworks/middleware 818 may provide various graphic user interface (GUI) functions, high-level resource management, high-level location services, and so forth. The frameworks/middleware 818 may provide a broad spectrum of other APIs that may be utilized by the applications 816 and/or other software components/modules, some of which may be specific to a particular operating system 802 or platform.

The applications 816 include built-in applications 838 and/or third-party applications 840. Examples of representative built-in applications 838 may include, but are not limited to, a contacts application, a browser application, a book reader application, a location application, a media application, a messaging application, and/or a game application. Third-party applications 840 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 840 may invoke the API calls 808 provided by the mobile operating system (such as operating system 802) to facilitate functionality described herein.

The applications 816 may use built in operating system functions (e.g., kernel 822, services 824 and/or drivers 826), libraries 820, and frameworks/middleware 818 to create user interfaces to interact with users of the system. Alternatively, or additionally, in some systems interactions with a user may occur through a presentation layer, such as presentation layer 814. In these systems, the application/component "logic" can be separated from the aspects of the application/component that interact with a user.

Figure 9:
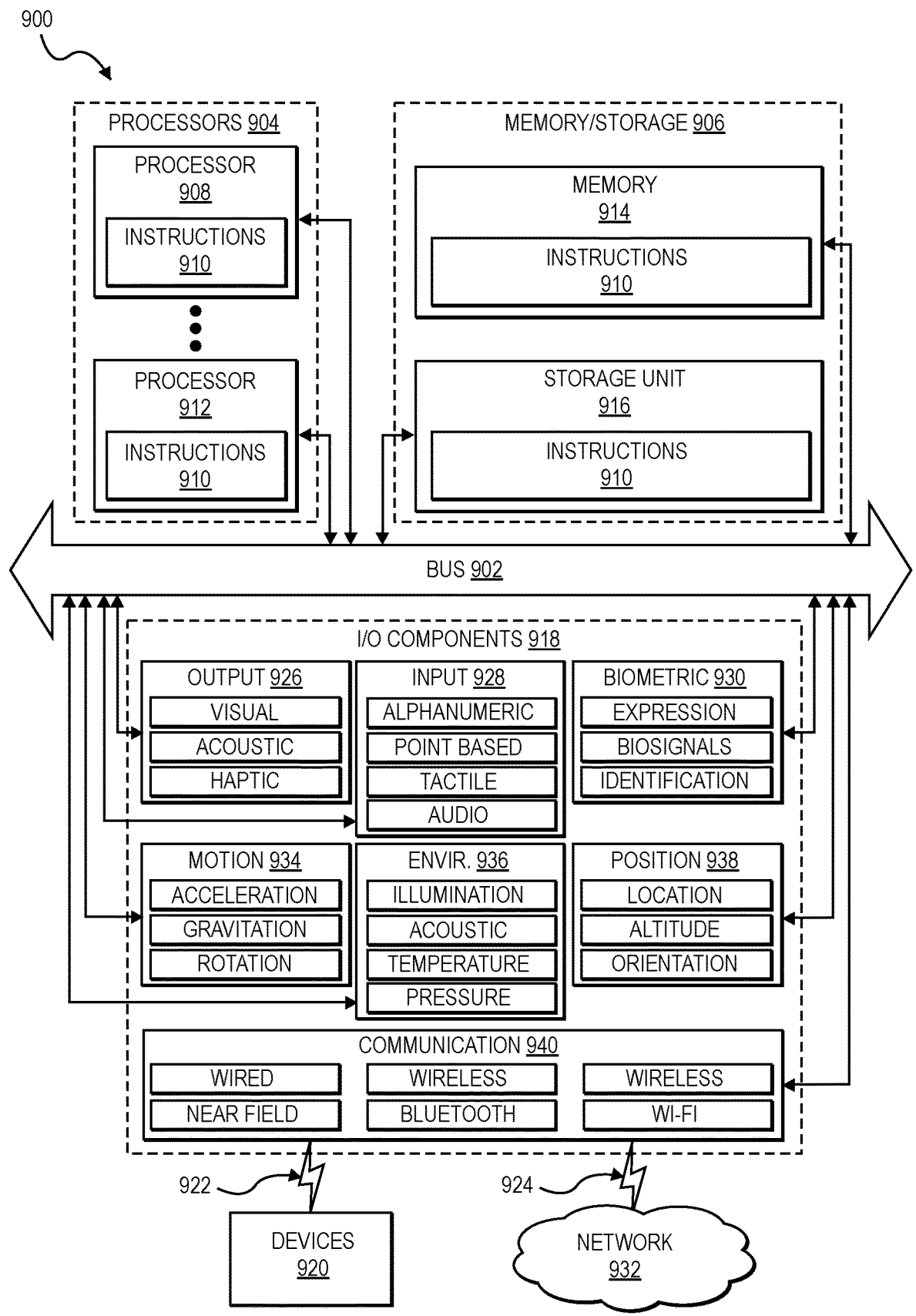
FIG. 9 is a block diagram illustrating components of an exemplary computer system according to some exemplary embodiments, which may read instructions from a machine-readable medium (e.g., a non-transitory computer-readable medium) and perform any one or more of the processes and methodologies discussed herein.

FIG. 9 is a block diagram illustrating components of a machine 900, according to some exemplary embodiments, able to read instructions from a machine-readable medium (e.g., a computer-readable storage medium) and perform any of the processes, methods, and/or functionality discussed herein. Specifically, FIG. 9 shows a diagrammatic representation of the machine 900 in the exemplary form of a computer system, within which instructions 910 (e.g., software, a program, an application, an applet, an app, or other executable code) for causing the machine 900 to perform any one or more of the methodologies discussed herein may be executed. As such, the instructions 910 may be used to implement modules or components described herein. The instructions 910 transform the general, non-programmed machine 900 into a particular machine 900 programmed to carry out the described and illustrated functions in the manner described.

In some embodiments, the machine 900 operates as a standalone device or may be coupled (e.g., networked) to other machines. In a networked deployment, the machine 900 may operate in the capacity of a server machine or a client machine in a server-client network environment, or as a peer machine in a peer-to-peer (or distributed) network environment. The machine 900 may be or include, but is not limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 910, sequentially or otherwise, that specify actions to be taken by machine 900. Further, while only a single machine 900 is illustrated, the term "machine" or "computer system" shall also be taken to include a collection of machines or computer systems that individually or jointly execute the instructions 910 to perform any of the methodologies discussed herein.

The machine 900 may include processors 904 (e.g., processors 908 and 912), memory memory/storage 906, and I/O components 918, which may be configured to communicate with each other, such as via bus 902. The memory/storage 906 may include a memory 914, such as a main memory, or other memory storage, and a storage unit 916, both accessible to the processors 904 such as via the bus 902. In this context, a "processor" may refer to any circuit or virtual circuit (a physical circuit emulated by logic executing on an actual processor) that manipulates data values according to control signals (e.g., "commands", "op codes", "machine code", etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC) or any combination thereof. A processor may further be a multi-core processor having two or more independent processors (sometimes referred to as "cores") that may execute instructions contemporaneously.

The storage unit 916 and memory 914 store the instructions 910 embodying any one or more of the methodologies or functions described herein. The instructions 910 may also reside, completely or partially, within the memory 914, within the storage unit 916, within at least one of the processors 904 (e.g., within the processor's cache memory), or any suitable combination thereof, during execution thereof by the machine 900. Accordingly, the memory 914, the storage unit 916, and the memory of processors 904 are examples of machine-readable media.

In this context, "machine-readable medium" refers to a component, device or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 918 may include a wide variety of components to receive input, provide output, produce output, transmit information, exchange information, capture measurements, and so on. The specific I/O components 918 that are included in a particular machine 900 will depend on the type of machine. For example, portable machines such as mobile phones will likely include a touch input device or other such input mechanisms, while a headless server machine will likely not include such a touch input device. It will be appreciated that the I/O components 918 may include many other components that are not shown in FIG. 9. The I/O components 918 are grouped according to functionality merely for simplifying the following discussion and the grouping is in no way limiting. In various exemplary embodiments, the I/O components 918 may include output components 926 and input components 928. The output components 926 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 928 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like. Collectively, one or more of the I/O components 918 may be referred to as a "user interface" for receiving input, and displaying output, to a user. Additionally, the term "user interface" may be used in other contexts such as, for example, to describe a graphical user interface (e.g., a window displayed on a display screen to receive input from, and display output to, a user).

In further exemplary embodiments, the I/O components 918 may include biometric components 930, motion components 934, environmental environment components 936, or position components 938 among a wide array of other components. For example, the biometric components 930 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 934 may include acceleration sensor components (e.g., accelerometer), gravitation sensor components, rotation sensor components (e.g., gyroscope), and so forth. The environment components 936 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 938 may include location sensor components (e.g., a Global Position system (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 918 may include communication components 940 operable to couple the machine 900 to a network 932 or devices 920 via coupling 922 and coupling 924 respectively. For example, the communication components 940 may include a network interface component or other suitable device to interface with the network 932. In further examples, communication components 940 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 920 may be another machine or any of a wide variety of peripheral devices (e.g., a peripheral device coupled via a Universal Serial Bus (USB)).

Moreover, the communication components 940 may detect identifiers or include components operable to detect identifiers. For example, the communication components 940 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 940, such as, location via Internet Protocol (IP) geo-location, location via Wi-Fi® signal triangulation, location via detecting a NFC beacon signal that may indicate a particular location, and so forth.

Where a phrase similar to "at least one of A, B, or C," "at least one of A, B, and C," "one or more A, B, or C," or "one or more of A, B, and C" is used, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A method comprising:
   receiving, by a computer system from a first client computing device in communication with the computer system, a first electronic communication that includes a request to determine a conclusion, the request including data for determining the conclusion;
   retrieving, by the computer system from a memory coupled to the computer system, one or more rules associated with the conclusion;
   determining, by the computer system, the conclusion based on the data and the one or more rules;
   identifying, by the computer system based on the data and the one or more rules, a plurality of factors having influence on the determination of the conclusion;
   selecting, by the computer system, one or more factors of the plurality of factors to indicate in a second electronic communication;
   retrieving, by the computer system from the memory, a respective explanation for each of the respective one or more selected factors, the respective explanation associated with each respective factor's influence on the conclusion; and
   transmitting, by the computer system, the second electronic communication to a second client computing device that includes at least one of: an indication of the conclusion, and at least one of an indication of the selected one or more selected factors, and an indication of the one or more explanations associated with the one or more selected factors, in which the second electronic communication is configured to cause the second client computing device to present, on a display screen of the second client computing device, a graphical user interface (GUI) that includes at least one of: the indication of the conclusion, the indication of the one or more selected factors, and the indication of the one or more explanations, and in which the GUI includes, displayed on the display screen, the indication of the conclusion and a selectable link that, when selected by a user of the second client computing device, displays at least one of the indication of the one or more explanations and the indication of the one or more factors in conjunction with the indication of the conclusion on the display screen.

2. The method of claim 1, in which identifying the plurality of factors includes determining, for each respective factor in the plurality of factors, a respective weight associated with the respective factor's influence on the conclusion relative to the other factors in the plurality of factors.

3. The method of claim 2, in which the computer system selects a factor from the plurality of factors having a highest weight.

4. The method of claim 2, in which the computer system selects a subset of factors from the plurality of factors based on the weights of the factors in the subset, and in which each of the selected factors in the subset have a higher weight than any unselected factor in the plurality of factors.

5. The method of claim 2, in which determining the respective weight for a respective factor includes:
   identifying a plurality of likelihood indicators associated with the respective factor;
   determining a respective weight for each respective likelihood indicator; and
   determining the weight for the respective factor as the sum of the weights determined for each respective likelihood indicator.

6. The method of claim 1, in which presenting the GUI includes displaying the indication of the explanation, the indication of the factor, and the indication of the conclusion together simultaneously on the display screen.

7. The method of claim 1, in which the second electronic communication further includes information associated with the determination of the conclusion, and in which presenting the GUI includes displaying the indication of the one or more explanations and the indication of the one or more factors in conjunction with a selectable link that, when selected by a user of the second client computing device, displays the information associated with the determination of the conclusion on the display screen.

8. The method of claim 1, in which a list of candidate determination factors is further retrieved from a data structure stored in the memory, and the plurality of the factors is identified from the retrieved a list of candidate determination factors.

9. The method of claim 8, in which the data structure includes a respective order of evaluation indicator for each respective candidate determination factor, the order indicating a sequence in which the candidate determination factors are to be evaluated.

10. The method of claim 8, in which the data structure further includes a respective set of likelihood indicators for each respective candidate determination factor, and in which identifying a factor having influence on the determination of the conclusion includes:
    determining a respective weight for each respective likelihood indicator in the set of likelihood indicators; and
    determining a respective weight for the factor having influence on the determination of the conclusion, in which the respective weight is determined as a sum of the weights determined for each respective likelihood indicator.

11. The method of claim 1, in which at least a certain one of the presented explanations includes a proposed remedy for the event that the factor associated with the certain one of the presented explanations is undesirable to a user of the display screen.

12. The method of claim 1, in which presenting the GUI includes displaying the indication of the one or more explanations in conjunction with a selectable link that, when selected by a user of the second client computing device, presents an option to modify a setting associated with the proposed remedy on the display screen.

13. The method of claim 1, in which the second client computing device is the same as the first client computing device.

14. The method of claim 1, in which the second client computing device is distinct from the first client computing device.

* * * * *